United States Patent
Iwasaki et al.

(10) Patent No.: US 9,996,927 B2
(45) Date of Patent: Jun. 12, 2018

(54) ENDOSCOPE APPARATUS

(71) Applicant: OLYMPUS CORPORATION, Tokyo (JP)

(72) Inventors: Tomoki Iwasaki, Fuchu (JP); Ryuichi Yamazaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/586,693

(22) Filed: May 4, 2017

(65) Prior Publication Data
US 2017/0236280 A1 Aug. 17, 2017

Related U.S. Application Data

(63) Continuation of application No. PCT/JP2016/076592, filed on Sep. 9, 2016.

(30) Foreign Application Priority Data

Oct. 29, 2015 (JP) ................... 2015-213153

(51) Int. Cl.
A61B 1/05 (2006.01)
G06T 7/00 (2017.01)
(Continued)

(52) U.S. Cl.
CPC .............. G06T 7/0012 (2013.01); A61B 1/05 (2013.01); A61B 5/024 (2013.01); G06T 7/20 (2013.01)

(58) Field of Classification Search
CPC ......... A61B 1/05; A61B 5/024; G06T 7/0012; G06T 7/20
(Continued)

(56) References Cited

U.S. PATENT DOCUMENTS 8,858,432 B2 * 10/2014 Robertson ............ A61B 5/0031
128/903
2004/0042581 A1 * 3/2004 Okerlund ............ A61B 5/0456
378/4
(Continued)

FOREIGN PATENT DOCUMENTS

JP H10-0323326 A 12/1998
JP 2002-085344 A 3/2002
(Continued)

OTHER PUBLICATIONS

Bhuvanan K et al, A multi camera wireless capsule endoscopic system, 2013.*
(Continued)

Primary Examiner — Shan E Elahi
(74) Attorney, Agent, or Firm — Scully, Scott, Murphy & Presser, P.C.

(57) ABSTRACT

An endoscope apparatus includes: a detector configured to detect a movement of an organ that moves a subject and output a detection signal; an image pickup portion configured to pick up an image of the subject and output a plurality of picked-up images; and a freeze processing portion configured to calculate a movement evaluation value evaluated according to the detection signal of the detector for at least some of the plurality of picked-up images, and determine a still image from the plurality of picked-up images based on the evaluated movement evaluation value.

16 Claims, 13 Drawing Sheets

(51) Int. Cl.
*G06T 7/20* (2017.01)
*A61B 5/024* (2006.01)

(58) Field of Classification Search
USPC .......................................................... 348/150
See application file for complete search history.

(56) References Cited

U.S. PATENT DOCUMENTS

| | | | | |
|---|---|---|---|---|
| 2005/0267453 | A1* | 12/2005 | Wong | A61B 8/12 |
| | | | | 606/27 |
| 2007/0127771 | A1* | 6/2007 | Kaneda | G06T 1/0028 |
| | | | | 382/100 |
| 2009/0082644 | A1* | 3/2009 | Li | A61B 5/036 |
| | | | | 600/302 |
| 2012/0265030 | A1* | 10/2012 | Li | A61B 5/036 |
| | | | | 600/301 |
| 2012/0321759 | A1* | 12/2012 | Marinkovich | A61B 5/0531 |
| | | | | 426/231 |
| 2013/0100254 | A1* | 4/2013 | Morioka | H04N 13/0025 |
| | | | | 348/47 |
| 2014/0213850 | A1* | 7/2014 | Levy | A61B 1/00137 |
| | | | | 600/156 |

FOREIGN PATENT DOCUMENTS

| | | |
|---|---|---|
| JP | 2013-128723 A | 7/2013 |
| JP | 2013-240522 A | 12/2013 |

OTHER PUBLICATIONS

Gu et al, Design of endoscopic capsule with multiple cameras, Aug. 2015.*

* cited by examiner

FIG. 6

| IMAGE PICKUP FRAME | N | N-1 | N-2 | N-3 | N-4 | N-5 | N-6 | N-7 | N-8 | ... | N-59 | N-60 | ... |
|---|---|---|---|---|---|---|---|---|---|---|---|---|---|
| SIGNAL VALUE OF MOVEMENT SIGNAL | 0 | 0 | 0 | 1 | 1 | 1 | 1 | 0 | 0 | ... | 0 | 0 | ... |
| COLOR SHIFT AMOUNT | 212 | 178 | 360 | 218 | 194 | 280 | 218 | 148 | 202 | ... | 460 | 312 | ... |
| PRESERVATION IN MEMORY | Yes | Yes | Yes | Yes | Yes | Yes | Yes | Yes | Yes | ... | Yes | Yes | ... |
| WEIGHTING COEFFICIENT | 0.5 | 0.5 | 0.5 | — | — | — | — | 0.5 | 0.5 | ... | 0.5 | 0.5 | ... |
| MOVEMENT EVALUATION VALUE | 106 | 89 | 180 | 218 | 194 | 280 | 218 | 74 | 101 | ... | 230 | 156 | ... |

FIG. 7

| IMAGE PICKUP FRAME | N | N−1 | N−2 | N−3 | N−4 | N−5 | N−6 | N−7 | N−8 | ... | N−59 | N−60 | ... |
|---|---|---|---|---|---|---|---|---|---|---|---|---|---|
| MOVEMENT EVALUATION VALUE | 106 | 89 | 180 | 218 | 194 | 280 | 218 | 74 | 101 | ... | 230 | 156 | ... |
| SIGNAL VALUE OF MOVEMENT SIGNAL | 0 | 0 | 0 | 1 | 1 | 1 | 1 | 0 | 0 | ... | 0 | 0 | ... |

| IMAGE PICKUP FRAME | N+1 | N | N−1 | N−2 | N−3 | N−4 | N−5 | N−6 | N−7 | ... | N−58 | N−59 | ... |
|---|---|---|---|---|---|---|---|---|---|---|---|---|---|
| MOVEMENT EVALUATION VALUE | 102 | 106 | 89 | 180 | 218 | 194 | 280 | 218 | 74 | ... | 198 | 230 | ... |
| SIGNAL VALUE OF MOVEMENT SIGNAL | 0 | 0 | 0 | 0 | 1 | 1 | 1 | 1 | 0 | ... | 0 | 0 | ... |

| IMAGE PICKUP FRAME | N+2 | N+1 | N | N−1 | N−2 | N−3 | N−4 | N−5 | N−6 | ... | N−57 | N−58 | ... |
|---|---|---|---|---|---|---|---|---|---|---|---|---|---|
| MOVEMENT EVALUATION VALUE | 71 | 102 | 106 | 89 | 180 | 218 | 194 | 280 | 218 | ... | 201 | 198 | ... |
| SIGNAL VALUE OF MOVEMENT SIGNAL | 0 | 0 | 0 | 0 | 0 | 1 | 1 | 1 | 1 | ... | 0 | 0 | ... |

| IMAGE PICKUP FRAME | N | N-1 | N-2 | N-3 | N-4 | N-5 | N-6 | N-7 | N-8 | ... | N-59 | N-60 | ... |
|---|---|---|---|---|---|---|---|---|---|---|---|---|---|
| SIGNAL VALUE OF MOVEMENT SIGNAL | 0 | 0 | 0 | 1 | 1 | 1 | 1 | 0 | 0 | ... | 0 | 0 | ... |
| COLOR SHIFT AMOUNT | 212 | 178 | 360 | — | — | — | — | 148 | 202 | ... | 460 | 312 | ... |
| PRESERVATION IN MEMORY | Yes | Yes | Yes | No | No | No | No | Yes | Yes | ... | Yes | Yes | ... |
| WEIGHTING COEFFICIENT | 0.5 | 0.5 | 0.5 | — | — | — | — | 0.5 | 0.5 | ... | 0.5 | 0.5 | ... |
| MOVEMENT EVALUATION VALUE | 106 | 89 | 180 | — | — | — | — | 74 | 101 | ... | 230 | 156 | ... |

| IMAGE PICKUP FRAME | N | N-1 | N-2 | N-3 | N-4 | N-5 | N-6 | N-7 | ... |
|---|---|---|---|---|---|---|---|---|---|
| SIGNAL VALUE OF MOVEMENT SIGNAL | 0 | 0 | 0 | 1 | 1 | 1 | 1 | 0 | ... |
| COLOR SHIFT AMOUNT | 100 | 110 | 130 | 90 | 110 | 120 | 100 | 120 | ... |
| PRESERVATION IN MEMORY | Yes | Yes | Yes | Yes | Yes | Yes | Yes | Yes | ... |
| WEIGHTING COEFFICIENT | 0.8 | 0.8 | 0.8 | 1 | 1 | 1 | 1 | 0.8 | ... |
| MOVEMENT EVALUATION VALUE | 80 | 88 | 104 | 90 | 110 | 120 | 100 | 96 | ... |

ENDOSCOPE APPARATUS

CROSS REFERENCE TO RELATED APPLICATION

This application is a continuation application of PCT/JP2016/076592 filed on Sep. 9, 2016 and claims benefit of Japanese Application No. 2015-213153 filed in Japan on Oct. 29, 2015, the entire contents of which are incorporated herein by this reference.

BACKGROUND OF THE INVENTION

1. Field of the Invention

The present invention relates to an endoscope apparatus.

2. Description of the Related Art

Conventionally, for example, as illustrated in Japanese Patent Application Laid-Open Publication No. 10-323326, there has been an endoscope apparatus capable of outputting a freeze image for which a movie is made to stand still.

The conventional endoscope apparatus picks up images by a frame-sequential method of successively picking up respective images of red, green and blue (abbreviated as "RGB" hereinafter), superimposing the respective images of the RGB and combining the images into one image, so as to observe a subject in a higher resolution. When the image of a moving subject is picked up by the frame-sequential method, sometimes the subject moves before pickup of the respective images of the RGB is completed, causing a color shift. In the conventional endoscope apparatus, a technique of calculating a color shift amount from shifts of edges of respective colors and outputting the image with a minimum color shift amount in a movie as a freeze image has been proposed.

SUMMARY OF THE INVENTION

An endoscope apparatus of one aspect of the present invention includes: a detector configured to detect a movement of an organ that moves a subject and output a detection signal; an image pickup portion configured to pick up an image of the subject and output a plurality of picked-up images; and a freeze processing portion configured to calculate a movement evaluation value evaluated according to the detection signal of the detector for at least some of the plurality of picked-up images, and determine a still image from the plurality of picked-up images based on the evaluated movement evaluation value.

BRIEF DESCRIPTION OF THE DRAWINGS

FIG. 6 is an explanatory diagram explaining the evaluation processing in the freeze processing portion of the endoscope apparatus, relating to the first embodiment of the present invention;

FIG. 7 is an explanatory diagram explaining a data structure of the memory of the endoscope apparatus, relating to the first embodiment of the present invention;

FIG. 8 is an explanatory diagram explaining the data structure of the memory of the endoscope apparatus, relating to the first embodiment of the present invention;

FIG. 9 is an explanatory diagram explaining the data structure of the memory of the endoscope apparatus, relating to the first embodiment of the present invention;

FIG. 11 is an explanatory diagram explaining the evaluation processing in the freeze processing portion of the endoscope apparatus, relating to a modification 1 of the first embodiment of the present invention;

FIG. 12 is an explanatory diagram explaining the evaluation processing in the freeze processing portion of the endoscope apparatus, relating to a modification 2 of the first embodiment of the present invention;

DETAILED DESCRIPTION OF THE PREFERRED EMBODIMENTS

Hereinafter, embodiments of the present invention will be described with reference to the drawings.

(First Embodiment)

Figure 1:
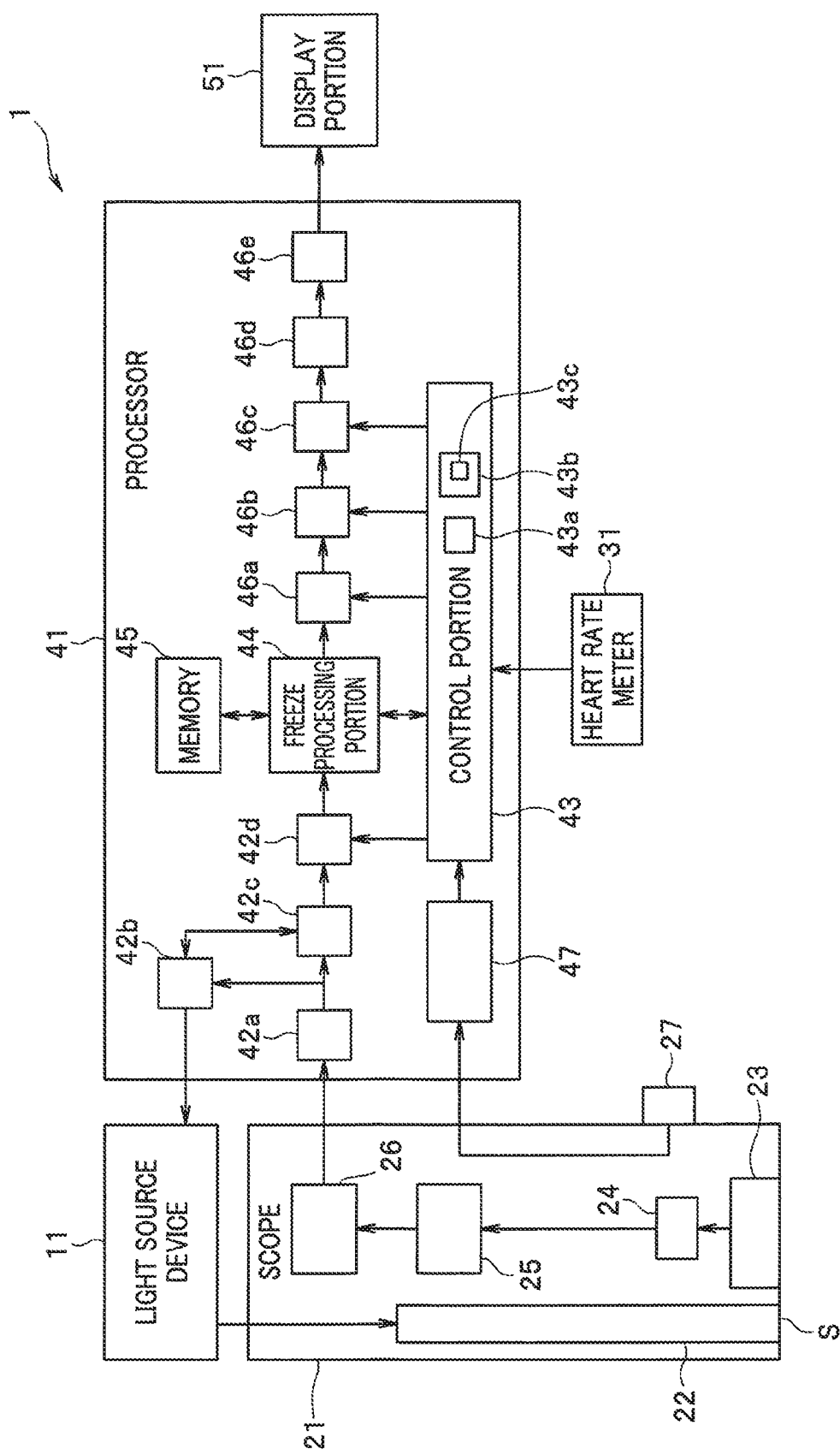
FIG. 1 is a block diagram illustrating a configuration of an endoscope apparatus, relating to a first embodiment of the present invention.

FIG. 1 is a block diagram illustrating a configuration of an endoscope apparatus 1, relating to the first embodiment of the present invention.

The endoscope apparatus 1 is configured including a light source device 11, a scope 21 which is an image pickup portion, a heart rate meter 31 which is a detector, a processor 41, and a display portion 51.

The light source device 11 is provided with a light source lamp and an RGB rotation filter, not shown in the figure. Illumination light radiated from the light source lamp becomes frame-sequential illumination light for which RGB cyclically changes, by interposing the RGB rotation filter that is rotationally driven. The frame-sequential illumination light is guided to a light guide 22 to be described later.

The scope 21 is configured including the light guide 22, an objective lens 23, a CCD 24, a correlated double sampling circuit (referred to as "CDS" hereinafter) 25, an AD conversion circuit 26, and a freeze switch 27. The scope 21 is configured such that a distal end is inserted into a body of a patient to pick up an image of a subject inside the body of the patient in an RGB frame-sequential manner and output a plurality of picked-up images to the processor 41.

The light guide 22 guides the frame-sequential illumination light radiated from the light source device 11, and irradiates the subject from a scope distal end face S.

The objective lens 23 fetches reflected light of the subject irradiated with the illumination light, and makes the CCD 24 form the image.

The CCD 24 is configured by an image pickup device capable of photoelectric conversion. The CCD 24 is connected to the CDS 25, converts the image-formed reflected light of the subject to an image pickup signal, and outputs the image pickup signal to the CDS 25.

The CDS 25 is a circuit configured to eliminate noise by correlated double sampling. The CDS 25 is connected to the AD conversion circuit 26, eliminates the noise from the image pickup signal inputted from the CCD 24, and outputs the image pickup signal to the AD conversion circuit 26.

The AD conversion circuit 26 is connected to the processor 41, and outputs the image pickup signal converted to a digital signal to the processor 41.

The freeze switch 27 is configured such that a user can input an instruction to start freeze processing. The freeze switch 27 is connected to the processor 41, and when the instruction to start the freeze processing is inputted by the user, outputs a control signal for starting the freeze processing to the processor 41.

The heart rate meter 31 which is the detector is configured to detect a movement of an organ that moves the subject and output a detection signal. More specifically, the heart rate meter 31 is configured to detect the movement of a heart that moves the subject such as an esophagus by a heart rate, for example. The heart rate meter 31 is configured, for example, to clamp a finger of a patient by a clip type probe not shown in the figure, measure a blood flow of the finger of the patient by an infrared ray sensor, and detect the heart rate. The heart rate meter 31 is connected to the processor 41. The heart rate meter 31 detects the movement of the heart, and outputs the detection signal to the processor 41.

The processor 41 is configured including a synchronization circuit 42a, a light adjustment detection circuit 42b, an automatic gain control circuit (referred to as "AGC circuit", hereinafter) 42c, a white balance circuit (referred to as "WB circuit", hereinafter) 42d, a control portion 43, a freeze processing portion 44, a memory 45, a gamma correction circuit 46a, a magnification/reduction circuit 46b, a contour emphasis circuit 46c, a matrix circuit (referred to as "MAT circuit" hereinafter) 46d, a DA conversion circuit 46e, and a scope communication control portion 47.

The synchronization circuit 42a is a circuit configured to synchronize the frame-sequential image pickup signal, and convert the image pickup signal to an image pickup frame which is a picked-up image. The synchronization circuit 42a is connected to the light adjustment detection circuit 42b and the AGC circuit 42c, synchronizes the frame-sequential image pickup signal inputted from the AD conversion circuit 26 to convert the image pickup signal to the image pickup frame, and outputs the image pickup frame to the light adjustment detection circuit 42b and the AGC circuit 42c.

The light adjustment detection circuit 42b is connected to the light source device 11, the AGC circuit 42c, and the control portion 43. The light adjustment detection circuit 42b outputs a control signal for adjusting brightness of the illumination light to the light source device 11 based on the brightness of the image pickup frame inputted from the synchronization circuit 42a. In addition, the light adjustment detection circuit 42b outputs a control signal for automatic gain control to the AGC circuit 42c.

The AGC circuit 42c is a circuit configured to automatically control gain. The AGC circuit 42c is connected to the WB circuit 42d, adjusts the gain of the image pickup frame inputted from the AD conversion circuit 26 based on the control signal inputted from the light adjustment detection circuit 42b, and outputs the image pickup frame to the WB circuit 42d.

The WB circuit 42d is a circuit configured to adjust white balance. The WB circuit 42d is connected to the freeze processing portion 44, adjusts the white balance for the image pickup frame inputted from the AGC circuit 42c under control of the control portion 43, and outputs the image pickup frame to the freeze processing portion 44.

The scope communication control portion 47 is a circuit configured to control communication with the scope 21. The scope communication control portion 47 is connected to the control portion 43, and when a freeze instruction signal is inputted from the freeze switch 27, outputs the freeze instruction signal to the control portion 43.

Figure 2:
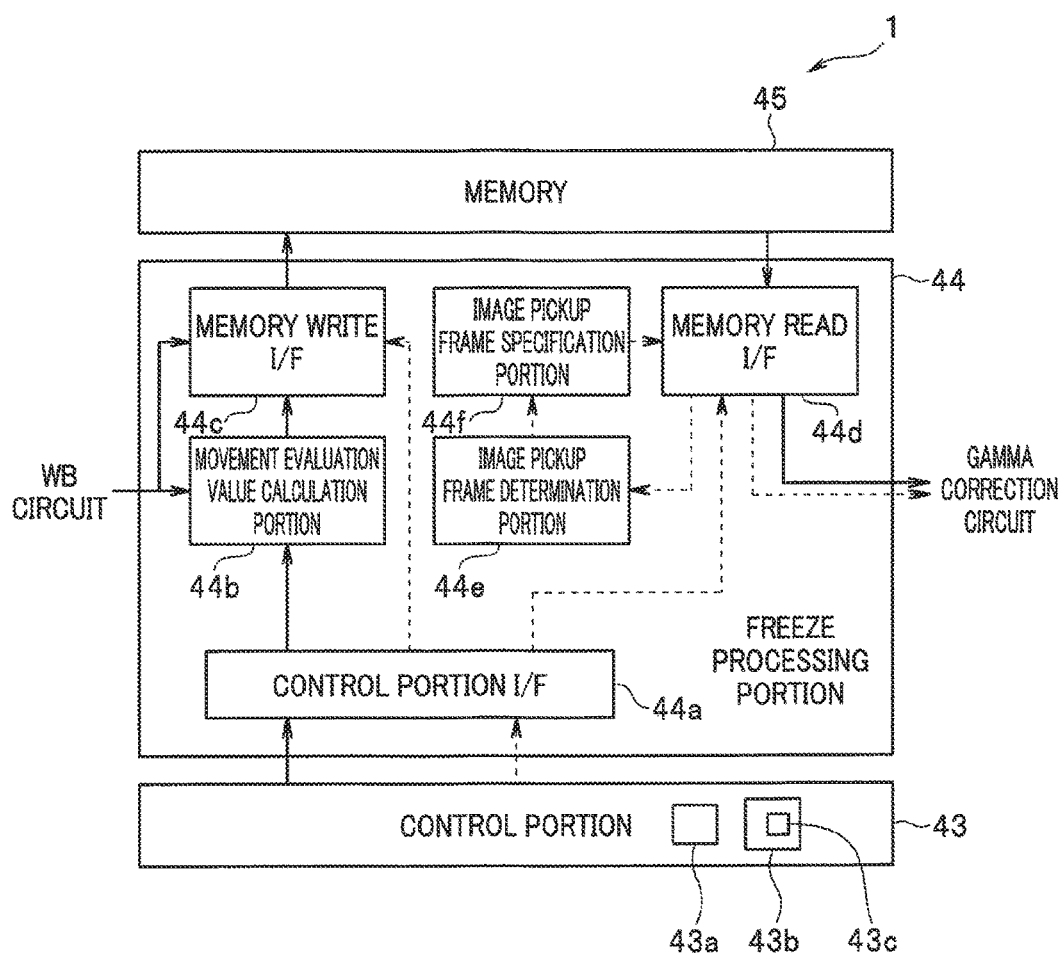
FIG. 2 is a block diagram illustrating a configuration of a CPU, a freeze processing portion and a memory of the endoscope apparatus, relating to the first embodiment of the present invention.
Figure 3:
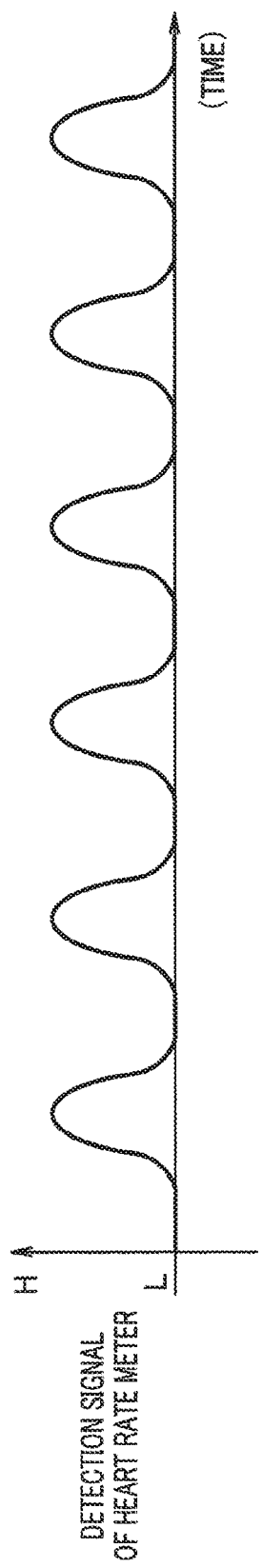
FIG. 3 is an explanatory diagram explaining an example of an input waveform of a detection signal of a heart rate meter of the endoscope apparatus, relating to the first embodiment of the present invention.
Figure 4:
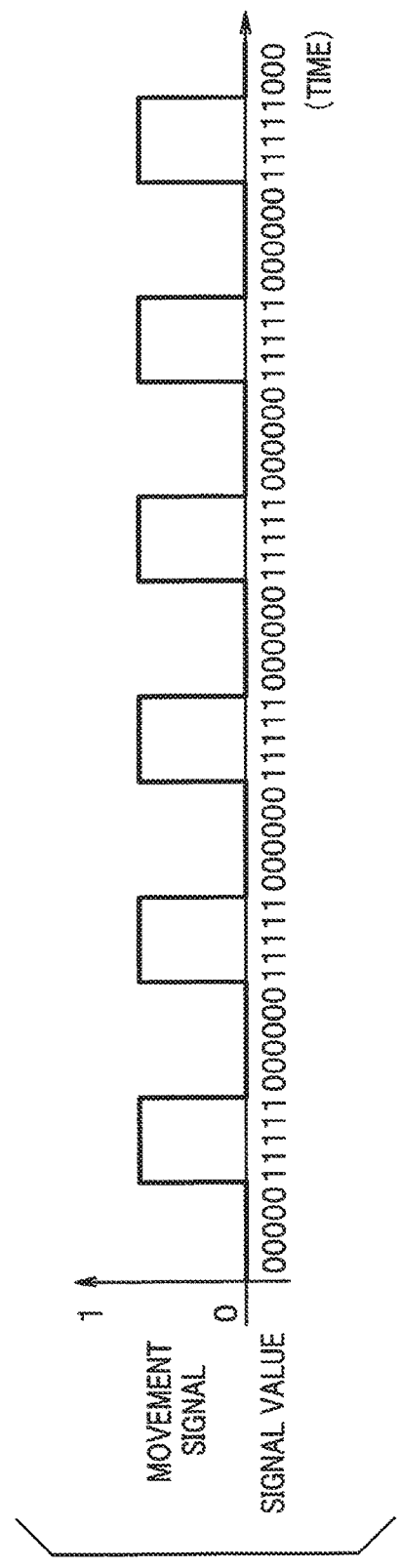
FIG. 4 is an explanatory diagram explaining a movement signal of the endoscope apparatus, relating to the first embodiment of the present invention.

FIG. 2 is a block diagram illustrating a configuration of a CPU 43a, the freeze processing portion 44 and the memory 45 of the endoscope apparatus 1, relating to the first embodiment of the present invention. In FIG. 2, a flow of processing in evaluation processing is indicated by a solid line, and a flow of processing in freeze processing is indicated by a broken line. FIG. 3 is an explanatory diagram explaining an example of an input waveform of the detection signal of the heart rate meter 31 of the endoscope apparatus 1, relating to the first embodiment of the present invention. FIG. 4 is an explanatory diagram explaining a movement signal of the endoscope apparatus 1, relating to the first embodiment of the present invention.

The control portion 43 is configured including a central processing unit (referred to as "CPU" hereinafter) 43a, and a storage portion 43b configured including a ROM and a RAM. A function of the CPU 43a is realized by executing various kinds of programs related to control processing stored in the storage portion 43b.

The CPU 43a is connected to the WB circuit 42d, the freeze processing portion 44, the gamma correction circuit 46a, the magnification/reduction circuit 46b, and the contour emphasis circuit 46c, and controls operations of the respective portions and the respective circuits.

When the freeze instruction signal is received from the scope communication control portion 47, the CPU 43a outputs the freeze instruction signal to the freeze processing portion 44.

The CPU 43a is connected to the heart rate meter 31, and the detection signal of the heart rate meter 31 is inputted.

In the storage portion 43b, the program from a movement signal processing portion 43c is stored.

The movement signal processing portion 43c is a processing portion configured to generate the movement signal based on the detection signal inputted from the heart rate meter 31.

The movement signal is configured having a signal value corresponding to each of the plurality of image pickup frames. The movement signal processing portion 43c sets a first signal value to the movement signal when a movement amount of the organ is smaller than a predetermined amount, and sets a second signal value to the movement signal when the movement amount of the heart is larger than the predetermined amount. More specifically, the movement signal processing portion 43c sets the first signal value to the movement signal when a signal value of the detection signal is smaller than a predetermined value V, and sets the second signal value to the movement signal when the signal value of the detection signal is larger than the predetermined value V. The predetermined value V is adjusted and preset to a value capable of excluding images not suitable for a freeze image.

For example, in the example of the input waveform of the detection signal in FIG. 3, the signal value of the detection signal becomes high (a peak section of the input waveform in FIG. 3) when the movement amount of the heart is large, and the detection signal becomes low (a valley section of the input waveform in FIG. 3) when the movement amount of the heart is small. For example, in FIG. 4, the first signal value "0" is set at the valley section of the input waveform, and the second signal value "1" is set at the peak section of the input waveform.

The movement signal generated by the movement signal processing portion 43c is outputted to the freeze processing portion 44.

The freeze processing portion 44 is configured including a control portion I/F 44a, a movement evaluation value calculation portion 44b, a memory write I/F 44c, a memory read I/F 44d, an image pickup frame determination portion 44e, and an image pickup frame specification portion 44f. The freeze processing portion 44 calculates a movement evaluation value evaluated according to the detection signal of the heart rate meter 31 for at least some of the plurality of image pickup frames, and determines a still image from the plurality of image pickup frames based on the evaluated movement evaluation value.

The control portion I/F 44a is a circuit for inputting various kinds of signals from the control portion 43. The control portion I/F 44a is connected to the movement evaluation value calculation portion 44b, the memory write I/F 44c, and the memory read I/F 44d. The control portion I/F 44a outputs the movement signal inputted from the control portion 43 to the movement evaluation value calculation portion 44b. The control portion I/F 44a outputs the freeze instruction signal inputted from the control portion 43 to the memory write I/F 44c and the memory read I/F 44d.

The movement evaluation value calculation portion 44b is a circuit configured to calculate the movement evaluation value for each of the plurality of image pickup frames. The movement evaluation value calculation portion 44b is connected to the memory write I/F 44c, and outputs the calculated movement evaluation value to the memory write I/F 44c.

The memory write I/F 44c is a circuit configured to output the image pickup frame inputted from the WB circuit 42d and the movement evaluation value and the signal value of the movement signal inputted from the movement evaluation value calculation portion 44b to the memory 45 to be stored. When the freeze instruction signal is inputted from the control portion 43 through the control portion I/F 44a, the memory write I/F 44c stops output of the image pickup frame, the movement evaluation value and the signal value of the movement signal to the memory 45.

The memory read I/F 44d is a circuit configured to read the image pickup frame, the movement evaluation value and the signal value of the movement signal stored in the memory 45. The memory read I/F 44d is connected to the gamma correction circuit 46a and the image pickup frame determination portion 44e.

The memory read I/F 44d instantly reads the image pickup frame stored in the memory 45 through the memory write I/F 44c and outputs the image pickup frame to the gamma correction circuit 46a, in the evaluation processing.

The memory read I/F 44d reads all the movement evaluation values and the signal values of the movement signal stored in the memory 45 and outputs the values to the image pickup frame determination portion 44e, in the freeze processing. In addition, in the freeze processing, when the image pickup frame is specified by the image pickup frame specification portion 44f, the memory read I/F 44d reads the image pickup frame from the memory 45, and outputs the image pickup frame to the gamma correction circuit 46a.

The image pickup frame determination portion 44e is a circuit configured to determine a minimum movement evaluation value from the plurality of movement evaluation values. The image pickup frame determination portion 44e determines the minimum movement evaluation value, and outputs a judgement result to the image pickup frame specification portion 44f.

The image pickup frame specification portion 44f is a circuit configured to specify the image pickup frame to the memory read I/F 44d. The image pickup frame specification portion 44f specifies the image pickup frame corresponding to the minimum movement evaluation value to the memory read I/F 44d, based on the judgement result inputted from the image pickup frame determination portion 44e.

The memory 45 is configured by a RAM or a nonvolatile memory to/from which various kinds of data related to the evaluation processing and the freeze processing can be written and read. In the memory 45, the image pickup frame, the movement evaluation value corresponding to the image pickup frame and the signal value of the movement signal are successively stored.

Returning to FIG. 1, the gamma correction circuit 46a is a circuit configured to perform gamma correction to the image pickup frame. The gamma correction circuit 46a is connected to the magnification/reduction circuit 46b, performs gamma correction processing to the image pickup frame inputted from the freeze processing portion 44 under the control of the control portion 43, and outputs the image pickup frame to the magnification/reduction circuit 46b.

The magnification/reduction circuit 46b is a circuit configured to perform magnification/reduction processing to the image pickup frame. The magnification/reduction circuit 46b is connected to the contour emphasis circuit 46c, performs the magnification/reduction processing to the image pickup frame inputted from the gamma correction circuit 46a under the control of the control portion 43, and outputs the image pickup frame to the contour emphasis circuit 46c.

The contour emphasis circuit 46c is a circuit configured to perform contour emphasis processing to the image pickup frame. The contour emphasis circuit 46c is connected to the MAT circuit 46d, performs the contour emphasis processing to the image pickup frame inputted from the magnification/reduction circuit 46b under the control of the control portion 43, and outputs the image pickup frame to the MAT circuit 46d.

The MAT circuit 46d is a circuit configured to generate the image to be outputted to the display portion 51. The MAT circuit 46d is connected to the DA conversion circuit 46e, generates display image data to be outputted to the display portion 51 from the image pickup frame outputted from the contour emphasis circuit 46c, and outputs the display image data to the DA conversion circuit 46e.

The DA conversion circuit 46e is a circuit configured to convert the digital signal to an analog signal. The DA conversion circuit 46e is connected to the display portion 51, converts the display image data inputted from the MAT circuit 46d to the analog signal, and outputs the analog signal to the display portion 51.

The display portion 51 displays the image on a screen based on the display image data outputted from the DA conversion circuit 46e.

(Operation of Freeze Processing Portion)

The flow of the evaluation processing of the freeze processing portion 44 in the first embodiment will be described.

Figure 5:
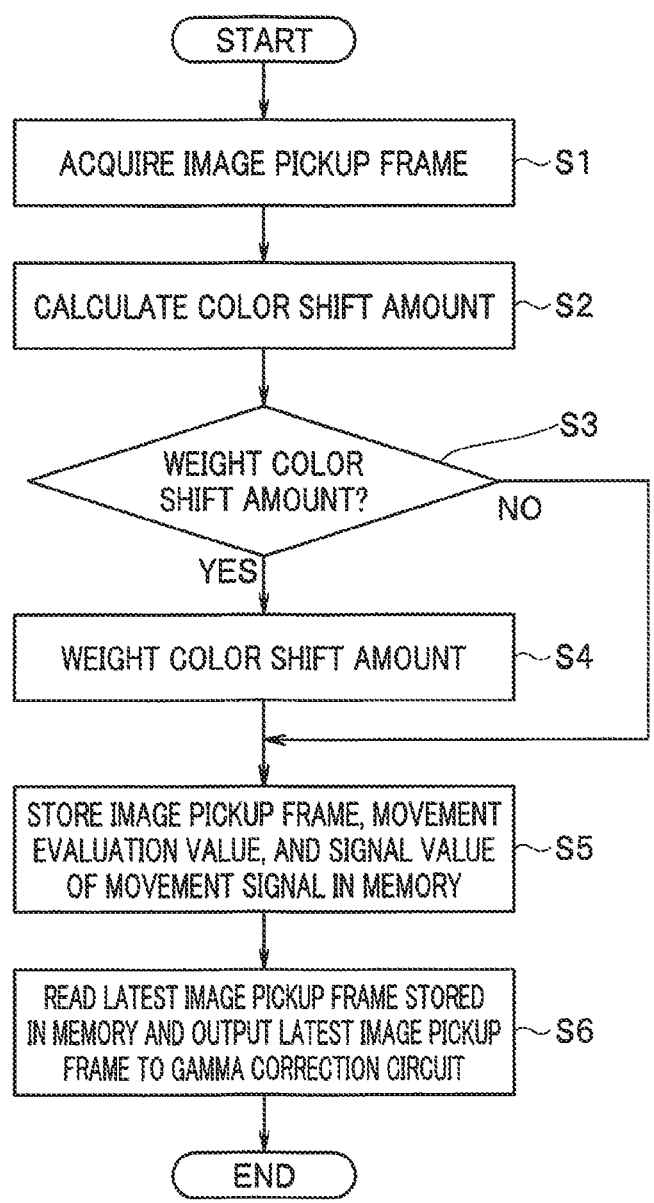
FIG. 5 is a flowchart illustrating an example of a flow of evaluation processing in the freeze processing portion of the endoscope, relating to the first embodiment of the present invention.

FIG. 5 is a flowchart illustrating an example of the flow of the evaluation processing in the freeze processing portion 44 of the endoscope 1, relating to the first embodiment of the present invention.

When the image of the subject is picked up by the scope 21 and the image pickup frame is inputted from the WB circuit 42d, the freeze processing portion 44 performs the evaluation processing.

The movement evaluation value calculation portion 44b acquires the image pickup frame (S1).

The movement evaluation value calculation portion 44b calculates a color shift amount (S2). In S2, the movement evaluation value calculation portion 44b calculates the color shift amount based on the image pickup frame inputted from the WB circuit 42d. The color shift amount is calculated by calculating an inclination value with an adjacent pixel for each pixel for the respective images of RGB and obtaining the number of the pixels having the different inclination value of a pixel value among the images of respective colors. For example, for the time when the image pickup frame is configured by 1024 pixels, when 900 pixels are present in which the inclination value with the adjacent pixel is the same among the RGB and 124 pixels are present in which the inclination value with the adjacent pixel is different from each other among the RGB, the color shift amount is 124. Note that a calculation method of the color shift amount described here is an example and the color shift amount may be calculated by other methods.

The movement evaluation value calculation portion 44b determines whether or not to weight the color shift amount (S3). In S3, the movement evaluation value calculation portion 44b acquires the signal value of the movement signal corresponding to the image pickup frame from the control portion 43 through the control portion I/F 44a, and determines whether or not to weight the color shift amount based on the signal value. The movement evaluation value calculation portion 44b determines to weight the color shift amount (S3: YES) when the signal value of the movement signal is the first signal value (for example, "0"), and the processing advances to S4. On the other hand, the movement evaluation value calculation portion 44b determines not to weight the color shift amount (S3: NO) when the signal value of the movement signal is the second signal value (for example, "1"), and the processing advances to S5.

In S4, the movement evaluation value calculation portion 44b weights the color shift amount. In S4, the movement evaluation value calculation portion 44b multiplies the color shift amount by a weighting coefficient, and weights the color shift amount. More specifically, when the signal value of the movement signal corresponding to the image pickup frame is the first signal value, the movement evaluation value calculation portion 44b multiplies the weighting coefficient and calculates the movement evaluation value. For example, when the color shift amount is 124 and the signal value of the movement signal is "0" which is the first signal value, when a weighting coefficient "0.5" is multiplied, the movement evaluation value becomes 62.

The weighting coefficient is adjusted and preset such that the image pickup frame for which a color shift and blurring are suppressed is appropriately determined in the image pickup frame determination portion 44e.

By the processing in S3 and S4, the movement evaluation value calculation portion 44b calculates the movement evaluation value by multiplying the color shift amount by the weighting coefficient in a case that the signal value of the movement signal is the first signal value, and calculates the movement evaluation value without multiplying the color shift amount by the weighting coefficient in the case that the signal value of the movement signal is the second signal value. That is, in the case that the signal value of the movement signal is the second signal value, the color shift amount becomes the movement evaluation value.

The movement evaluation value calculation portion 44b stores the image pickup frame, the movement evaluation value and the signal value of the movement signal in the memory 45 (S5). In S5, the movement evaluation value calculation portion 44b stores the image pickup frame, the movement evaluation value and the signal value of the movement signal correspond to each other in the memory 45 through the memory write I/F 44c.

The memory read I/F 44d reads a latest image pickup frame stored in the memory 45, and outputs the latest image pickup frame to the gamma correction circuit 46a (S6).

By repeating the evaluation processing from S1 to S6, on the memory 45, the image pickup frame and the movement evaluation value and the signal value of the movement signal corresponding to the image pickup frame are successively stored.

FIG. 6 is an explanatory diagram explaining the evaluation processing in the freeze processing portion 44 of the endoscope apparatus 1, relating to the first embodiment of the present invention.

For example, in FIG. 6, the latest image pickup frame acquired by the movement evaluation value calculation portion 44b is an image pickup frame N (S1), the color shift amount of the image pickup frame N is calculated to be "212" (S2), it is determined to weight the color shift amount since the signal value of the movement signal is the first signal value "0" (S3), the weighting coefficient "0.5" is multiplied, and a movement evaluation value "106" is calculated (S4). Note that, in the first embodiment, since all the image pickup frames are stored in the memory 45, in FIG. 6, "preservation in the memory" of the image pickup frame N is described as "Yes".

An image pickup frame N−1 is the image pickup frame acquired by the movement evaluation value calculation portion 44b one frame before the image pickup frame N, an image pickup frame N−2 is the image pickup frame acquired by the movement evaluation value calculation portion 44b two frames before the image pickup frame N, and descriptions are omitted.

An image pickup frame N−3 is the image pickup frame acquired by the movement evaluation value calculation portion 44b three frames before the image pickup frame N, the color shift amount of the image pickup frame is calculated to be "218", it is determined not to weight the color shift amount since the signal value of the movement signal is the second signal value "1" (S3), and a movement evaluation value "218" is calculated without multiplying the weighting coefficient.

For an image pickup frame N–4 to an image pickup frame N–8, an image pickup frame N–59 and an image pickup frame N–60, the descriptions are omitted.

FIG. 7, FIG. 8 and FIG. 9 are explanatory diagrams explaining data stored on the memory 45 of the endoscope apparatus 1, relating to the first embodiment of the present invention.

For example, in FIG. 7, the latest image pickup frame stored in the memory 45 is the image pickup frame N, the movement evaluation value is "106", and the signal value of the movement signal is "0". The image pickup frame N–1 is the image pickup frame stored one frame before the image pickup frame N, the movement evaluation value is "89", and the signal value of the movement signal is "0". In addition, the image pickup frame N–60 is the image pickup frame stored 60 frames before the image pickup frame N, the movement evaluation value is "156", and the signal value of the movement signal is "0". For the image pickup frame N–2 to the image pickup frame N–59, the descriptions are omitted.

FIG. 8 is an example in which an image pickup frame N+1, the movement evaluation value "102", and the signal value of the movement signal "0" are additionally stored in the memory 45 further. FIG. 9 is an example in which an image pickup frame N+2, the movement evaluation value "71", and the signal value of the movement signal "0" are additionally stored in the memory 45 further.

The processing in S1-S6 configures the evaluation processing.

Subsequently, the flow of the freeze processing in the freeze processing portion 44 in the first embodiment will be described.

Figure 10:
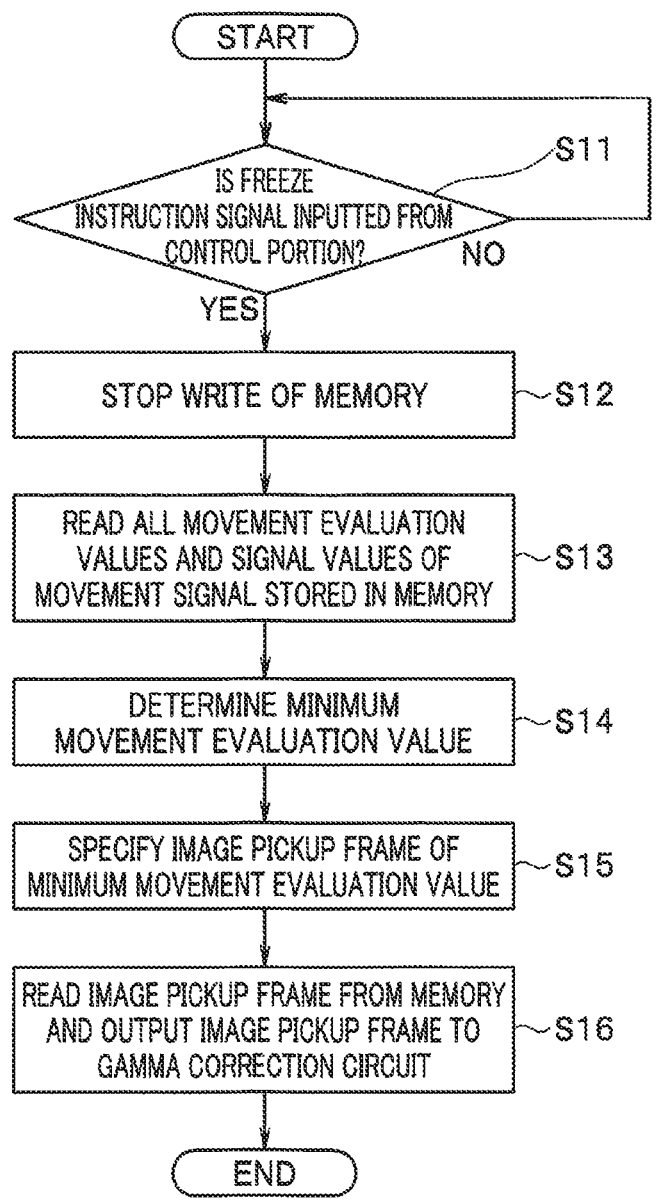
FIG. 10 is a flowchart illustrating an example of a flow of freeze processing in the freeze processing portion of the endoscope apparatus, relating to the first embodiment of the present invention.

FIG. 10 is a flowchart illustrating an example of the flow of the freeze processing in the freeze processing portion 44 of the endoscope apparatus 1, relating to the first embodiment of the present invention.

The control portion I/F 44a determines whether or not the freeze instruction signal is inputted from the control portion 43 (S11). When the freeze instruction signal is inputted from the control portion 43 (S1: YES), the processing advances to S12. On the other hand, when the freeze instruction signal is not inputted from the control portion 43 (S11: NO), the processing returns to S11. That is, the control portion I/F 44a stands by until the freeze instruction signal is inputted from the control portion 43.

The memory write I/F 44c stops write to the memory 45 (S12). In S12, the control portion I/F 44a transmits the freeze instruction signal to the memory write I/F 44c. When the freeze instruction signal is received, the memory write I/F 44c stops the write to the memory 45.

The memory read I/F 44d reads all the movement evaluation values and the signal values of the movement signal stored in the memory 45 (S13). In S13, the control portion I/F 44a transmits the freeze instruction signal to the memory read I/F 44d. When the freeze instruction signal is received, the memory read I/F 44d reads all the movement evaluation values and the signal values of the movement signal stored in the memory 45, and outputs the values to the image pickup frame determination portion 44e.

The image pickup frame determination portion 44e determines the minimum movement evaluation value (S14). In S14, in the image pickup frame determination portion 44e, the minimum movement evaluation value included in a predetermined number A of the movement evaluation values tracing back from all the movement evaluation values inputted from the memory 45 through the memory read I/F 44d is determined, and the judgement result is outputted to the image pickup frame specification portion 44f. The predetermined number A is adjusted and preset to be a number allowing acquisition of an optimum freeze image.

For example, when the predetermined number A is defined as 5, in a storage state of the memory 45 in FIG. 7, the image pickup frame determination portion 44e determines that the movement evaluation value "89" corresponding to the image pickup frame N–1 is minimum among the image pickup frame N to the image pickup frame N–4. For example, in the storage state of the memory 45 in FIG. 8, the image pickup frame determination portion 44e determines that the movement evaluation value "89" corresponding to the image pickup frame N–1 is the minimum among the movement evaluation values of the image pickup frames N+1 to N–3. For example, in the storage state of the memory 45 in FIG. 9, the image pickup frame determination portion 44e determines that the movement evaluation value "71" corresponding to the image pickup frame N+2 is the minimum among the movement evaluation values of the image pickup frames N+2 to N–2.

The image pickup frame specification portion 44f specifies the image pickup frame of the minimum movement evaluation value to the memory read I/F 44d (S15). In S15, the image pickup frame specification portion 44f extracts an address on the memory 45 of the image pickup frame corresponding to the minimum movement evaluation value from the judgement result inputted in S14, and outputs the address to the memory read I/F 44d.

The memory read I/F 44d reads the image pickup frame from the memory 45, and outputs the image pickup frame to the gamma correction circuit 46a (S16). In S16, the image pickup frame is read from the memory 45 based on the address inputted from the image pickup frame specification portion 44f in S15, and is outputted to the gamma correction circuit 46a.

The processing from S11 to S16 configures the flow of the freeze processing in the freeze processing portion 44.

According to the first embodiment described above, the still image for which the color shift and the blurring are suppressed can be outputted for the subject moved by the heart.

(Modification 1 of First Embodiment)

The image pickup frame determination portion 44e determines the minimum movement evaluation value without excluding the movement evaluation values for which the signal value of the movement signal is the second signal value in the first embodiment, however, the movement evaluation values for which the signal value of the movement signal is the second signal value may be excluded.

FIG. 11 is an explanatory diagram explaining the evaluation processing in the freeze processing portion 44 of the endoscope apparatus 1, relating to the modification 1 of the first embodiment of the present invention.

The image pickup frame determination portion 44e is configured to exclude the movement evaluation values for which the signal value of the movement signal is the second signal value (for example, "1") from all the movement evaluation values inputted from the memory 45 through the memory read I/F 44d in S13, determine the minimum movement evaluation value included in the predetermined number A of the movement evaluation values tracing back from the latest movement evaluation value, and output the judgement result to the image pickup frame specification portion 44f.

For example, when the predetermined number A is defined as 5, in the storage state of the memory 45 in FIG. 7, the image pickup frames N−3 to N−6 for which the signal value of the movement signal is the second signal value "1" are excluded, and the image pickup frame determination portion 44e determines that a movement evaluation value "74" corresponding to an image pickup frame N−7 is minimum among the movement evaluation values (a dashed line P1 in FIG. 7) of the image pickup frames N, N−1, N−2, N−7 and N−8. For example, in the storage state of the memory 45 in FIG. 8, the image pickup frame determination portion 44e determines that the movement evaluation value "74" corresponding to the image pickup frame N−7 is the minimum among the movement evaluation values (a dashed line P2 in FIG. 8) of the image pickup frames N+1, N, N−1, N−2 and N−7. For example, in the storage state of the memory 45 in FIG. 9, the image pickup frame determination portion 44e determines that the movement evaluation value "71" corresponding to the image pickup frame N+2 is the minimum among the movement evaluation values (a dashed line P3 in FIG. 9) of the image pickup frames N+2 to N−2.

Note that, in the modification 1 of the first embodiment described above, the movement evaluation values of the image pickup frames for which the signal value of the movement signal is the second signal value and which are excluded by the image pickup frame determination portion 44e are also stored in the memory 45, however, the movement evaluation value calculation portion 44b may not store the movement evaluation value in the memory 45 when the signal value of the movement signal is the second signal value. FIG. 11 is an example that the signal value of the movement signal is the second signal value "1" for the image pickup frame N−3 to the image pickup frame N−6, the color shift amount and the movement evaluation value are not calculated (a dashed line P4), and the movement evaluation value is not stored in the memory 45.

Note that, for the movement evaluation value of the image pickup frame to be excluded, for example, an arbitrary value such as "0" may be set.

According to the configuration of the modification 1 of the first embodiment described above, the movement evaluation value is excluded depending on the signal value of the movement signal, and the still image for which the color shift and the blurring are more surely suppressed can be outputted for the subject moved by the heart.

(Modification 2 of First Embodiment)

In the first embodiment and the modification 1 of the first embodiment, the movement evaluation value calculation portion 44b multiplies the weighting coefficient when the signal value of the movement signal is the first signal value, however, the weighting coefficient corresponding to each signal value may be multiplied when the signal value of the movement signal is the first signal value and the second signal value.

FIG. 12 is an explanatory diagram explaining the evaluation processing in the freeze processing portion 44 of the endoscope apparatus 1, relating to the modification 2 of the first embodiment of the present invention.

In the modification 2 of the first embodiment, the movement evaluation value calculation portion 44b is configured to calculate the movement evaluation value by multiplying a first weighting coefficient (for example, "0.8") when the signal value of the movement signal corresponding to the picked-up image is the first signal value (for example, "0"), and multiplying a second weighting coefficient (for example, "1") larger than the first weighting coefficient when the signal value of the movement signal is the second signal value (for example, "1").

For example, in the image pickup frame N in FIG. 12, the color shift amount is calculated to be "100", the weighting coefficient "0.8" is multiplied since the signal value of the movement signal is the first signal value "0", and a movement evaluation value "80" is calculated. In the image pickup frame N−3, the color shift amount is calculated to be "90", the weighting coefficient "1" is multiplied since the signal value of the movement signal is the second signal value "1", and a movement evaluation value "90" is calculated. For the other image pickup frames, the descriptions are omitted.

According to the configuration of the modification 2 of the first embodiment described above, for the subject moved by the heart, the evaluation processing is performed according to a binary movement signal, and the still image for which the color shift and the blurring are suppressed with higher accuracy can be outputted.

(Modification 3 of First Embodiment)

In the first embodiment, the modification 1 of the first embodiment and the modification 2 of the first embodiment, the signal value of the movement signal is binary and is the first signal value and the second signal value, however, the signal value of the movement signal may be ternary or have more values.

The modification 3 of the first embodiment is an example that the signal value of the movement signal is ternary.

The movement signal processing portion 43c is configured to set the first signal value to the movement signal when the movement amount of the organ is smaller than a first movement amount, set the second signal value to the movement signal when the movement amount of the organ is larger than the first movement amount and smaller than a second movement amount, and set a third signal value to the movement signal when the movement amount of the organ is larger than the second movement amount.

More specifically, the movement signal processing portion 43c is configured to set the first signal value to the movement signal when the signal value of the detection signal is smaller than a predetermined value W1 depending on the detection signal, set the second signal value to the movement signal when the signal value of the detection signal is larger than the predetermined value W1 and smaller than a predetermined value W2, and set a third signal value to the movement signal when the signal value of the detection signal is larger than the predetermined value W2. The predetermined values W1 and W2 are adjusted and preset to be the value allowing exclusion of the image not suitable for the freeze image.

The movement evaluation value calculation portion 44b is configured to calculate the movement evaluation value by multiplying the first weighting coefficient (for example, "0.5") when the signal value of the movement signal corresponding to the picked-up image is the first signal value, multiplying the second weighting coefficient (for example, "1") larger than the first weighting coefficient when the signal value is the second signal value, and multiplying a third weighting coefficient (for example, "2") larger than the second weighting coefficient when the signal value is a third signal value.

According to the configuration of the modification 3 of the first embodiment described above, for the subject moved by the heart, the evaluation processing is performed according to a ternary movement signal, and the still image for which the color shift and the blurring are suppressed with the higher accuracy can be outputted.

(Second Embodiment)

In the first embodiment, the modification 1 of the first embodiment, the modification 2 of the first embodiment and the modification 3 of the first embodiment, all the image pickup frames are stored in the memory 45, however, the image pickup frame may be stored in the memory 45 only when the signal value of the movement signal is a predetermined value.

Figure 13:
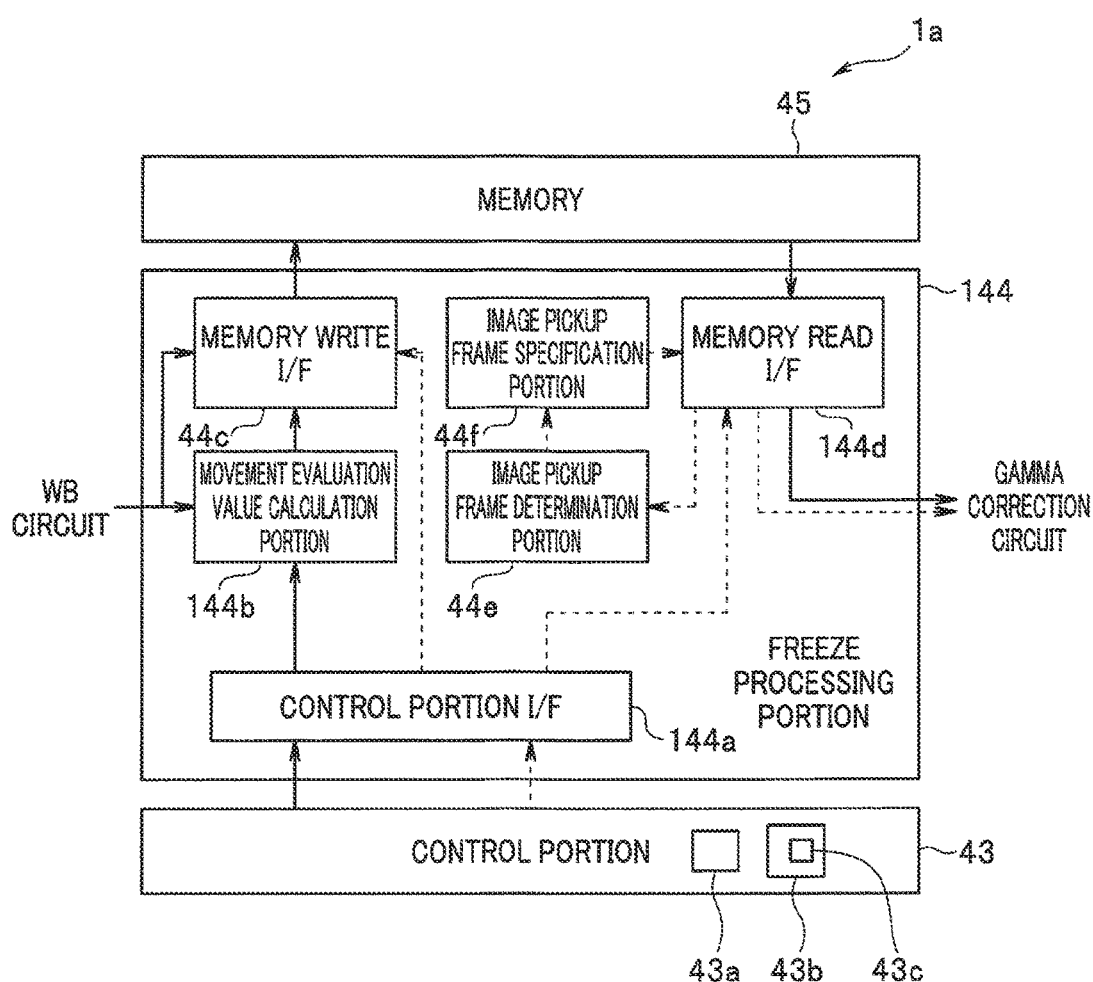
FIG. 13 is a block diagram illustrating a configuration of the CPU, the freeze processing portion and the memory of an endoscope apparatus, relating to a second embodiment of the present invention.
Figure 14:
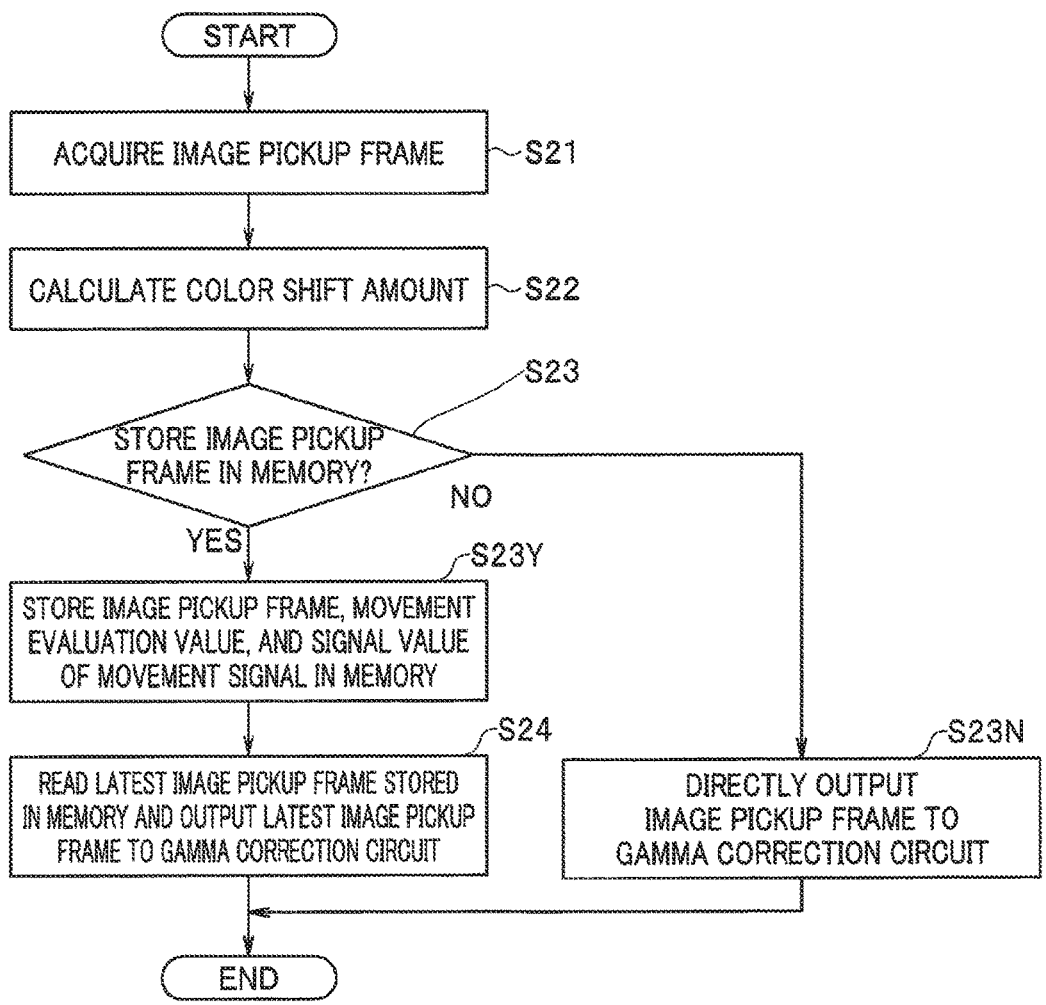
FIG. 14 is a flowchart illustrating an example of a flow of the evaluation processing in the freeze processing portion of the endoscope apparatus, relating to the second embodiment of the present invention.
Figure 15:
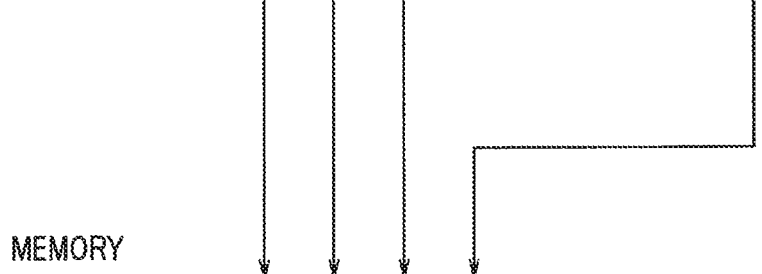
FIG. 15 is an explanatory diagram explaining the evaluation processing in the freeze processing portion of the endoscope apparatus, relating to the second embodiment of the present invention.

FIG. 13 is a block diagram illustrating a configuration of the CPU 43a, a freeze processing portion 144 and the memory 45 of an endoscope apparatus 1a, relating to the second embodiment of the present invention. FIG. 14 is a flowchart illustrating an example of the flow of the evaluation processing in the freeze processing portion 144 of the endoscope apparatus 1a, relating to the second embodiment of the present invention. FIG. 15 is an explanatory diagram explaining the evaluation processing in the freeze processing portion 144 of the endoscope apparatus 1a, relating to the second embodiment of the present invention. In the second embodiment, for components same as the components in the first embodiment, same signs are attached in FIG. 13, and the descriptions are omitted.

As illustrated in FIG. 13, a control portion I/F 144a is configured to output the movement signal inputted from the control portion 43 to a memory write I/F 144c.

When the signal value of the movement signal inputted from the control portion 43 through the control portion I/F 144a is the first signal value, the memory write I/F 144c outputs the image pickup frame inputted from the WB circuit 42d and the movement evaluation value and the signal value of the movement signal inputted from the movement evaluation value calculation portion 44b to the memory 45 to be stored. When the signal value of the movement signal is the second signal value, the memory write I/F 144c outputs the image pickup frame inputted from the WB circuit 42d directly to the gamma correction circuit 46a.

Hereinafter, the evaluation processing in the freeze processing portion 144 of the second embodiment will be described.

The movement evaluation value calculation portion 144b acquires the image pickup frame (S21).

The movement evaluation value calculation portion 144b calculates the color shift amount (S22).

The memory write I/F 144c determines whether or not to store the image pickup frame in the memory 45 (S23). In S23, the memory write I/F 144c acquires the signal value of the movement signal corresponding to the image pickup frame from the control portion 43 through the control portion I/F 144a, and determines whether or not to store the image pickup frame in the memory 45 based on the signal value. The memory read I/F 144d determines to store the image pickup frame in the memory 45 (S23: YES) when the signal value of the movement signal is the first signal value (for example, "0"), and the processing advances to S23Y. On the other hand, when the signal value of the movement signal is the second signal value (for example, "1"), it is determined that the image pickup frame is not to be stored in the memory 45 (S23: NO), and the processing advances to S23N.

In S23Y, the memory write I/F 144c stores the image pickup frame, the movement evaluation value and the signal value of the movement signal in the memory 45.

In S23N, the memory write I/F 144c directly outputs the image pickup frame to the gamma correction circuit 46a. After the processing in S23N, the evaluation processing ends.

In S24, the memory read I/F 144d reads the latest image pickup frame stored in the memory 45, and outputs the latest image pickup frame to the gamma correction circuit 46a. After the processing in S24, the evaluation processing ends.

For example, FIG. 15 is an example that, from the control portion I/F 144a to the memory write I/F 144c, the signal value "0" of the movement signal is inputted from the image pickup frame N to the image pickup frame N−2, the signal value "1" of the movement signal is inputted from the image pickup frame N−3 to the image pickup frame N−6, and the signal value "0" of the movement signal is inputted in the image pickup frame N−7 (an upper section of FIG. 15). The memory write I/F 144c stores the image pickup frames N, N−1, N−2 and N−7 which are the image pickup frames of the signal value "0" of the movement signal in the memory 45 together with the signal value of the movement signal and the movement evaluation value (S23Y in FIG. 14, a lower section of FIG. 15).

The processing from S21 to S24 configures the evaluation processing.

Since the operation of the freeze processing in the second embodiment is similar to the operation in the first embodiment, the descriptions are omitted.

According to the second embodiment described above, a storage amount of the memory 45 can be suppressed, and for the subject moved by the heart, the still image for which the color shift and the blurring are suppressed can be outputted.

(Modification 1 of the Second Embodiment)

In the second embodiment described above, the signal value of the movement signal is binary, however, the signal value of the movement signal may be ternary or have more values.

Figure 16:
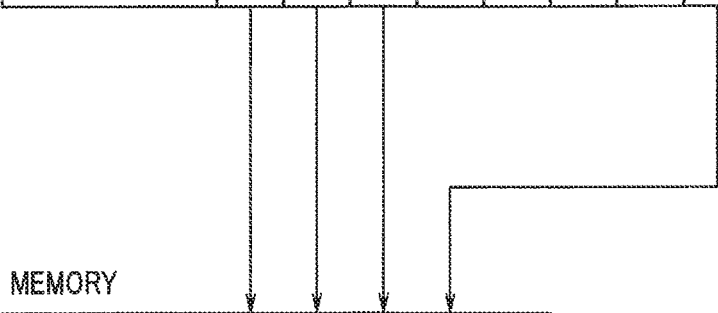
FIG. 16 is an explanatory diagram explaining the evaluation processing of the endoscope apparatus, relating to a modification 1 of the second embodiment of the present invention.

FIG. 16 is an explanatory diagram explaining the evaluation processing in the freeze processing portion 144 of the endoscope apparatus 1, relating to the modification 1 of the second embodiment of the present invention.

In the modification 1 of the second embodiment, the movement signal processing portion 43c is configured to set the first signal value to the movement signal when the signal value of the detection signal is smaller than the predetermined value W1 depending on the detection signal, set the second signal value to the movement signal when the signal value of the detection signal is larger than the predetermined value W1 and smaller than the predetermined value W2, and set the third signal value to the movement signal when the signal value of the detection signal is larger than the predetermined value W2.

The movement evaluation value calculation portion 144b is configured to multiply a fourth weighting coefficient (in FIG. 16, "0.8") when the signal value of the movement signal corresponding to the picked-up image is the first signal value (in FIG. 16, "0"), to multiply a fifth weighting coefficient (for example, "1") larger than the fourth weighting coefficient when the signal value is the second signal value (in FIG. 16, "1"), and not to store the image pickup frame in the memory 45 when the signal value is the third signal value (in FIG. 16, "2").

For example, in FIG. 16, for the image pickup frame N, the signal value of the movement signal is "0", the color shift amount is "100", the weighting coefficient is "0.8", and the movement evaluation value is "80" for which the color shift amount is multiplied by the weighting coefficient. In the image pickup frame N−2, the signal value of the movement signal is "1", the color shift amount is "130", the weighting coefficient is "1", and the movement evaluation value is "130". The image pickup frame N−3 is not stored in the memory 45 since the signal value of the movement signal is "2". The descriptions of the image pickup frames N–1, N–4, N–5, N–6 and N–7 are omitted.

According to the modification 1 of the second embodiment 2 described above, the storage amount of the memory 45 can be suppressed, the evaluation processing can be performed according to the ternary movement signal, and the still image for which the color shift and the blurring are suppressed with the higher accuracy can be outputted.

Note that, in the embodiment, the image is picked up by the frame-sequential method for the image pickup frame, and the movement evaluation value calculation portion 44b calculates the color shift amount which is an evaluation value, however, the image may be picked up by the image pickup device for which RGB pixels are arranged on a same plane for the image pickup frame, and the movement evaluation value calculation portion 44b may calculate a blurring amount which is the evaluation value.

Note that, in the embodiment, the heart rate meter 31 configured to detect the heart rate by the infrared ray sensor is described as an example of the heart rate meter 31, however, without being limited to such a heart rate meter 31, the heart rate meter may be any type as long as the heart rate of the patient can be detected, such as the heart rate meter configured to detect the heart rate by a voltage change.

Note that, in the embodiment, the subject is the esophagus and the organ that moves the subject is the heart, however, the subject may be something other than the esophagus, and the organ that moves the subject may be an organ other than the heart.

Note that, in the embodiment, the movement signal is generated by the detection signals inputted successively from the heart rate meter 31, however, the control portion 43 may generate a cyclic movement signal using some of the detection signals inputted from the heart rate meter 31.

The present invention is not limited to the embodiments described above, and various changes and modifications or the like are possible without changing a subject matter of the present invention.

According to the present invention, an object is to provide the endoscope apparatus capable of obtaining the still image for which the color shift and the blurring are suppressed, for the subject moved by the organ.

What is claimed is:
1. An endoscope apparatus comprising:
a heart rate sensor configured to contact a subject's skin and detect a movement of an organ of the subject and the sensor configured to output a detection signal of the organ;
an endoscope configured for insertion into the subject, the scope comprising an image sensor configured to capture a plurality of images of the organ; and
a processor comprising hardware, the processor operably connected to the heart rate sensor and the image sensor, the processor configured to:
receive a plurality of images, each of the plurality of images captured by the image sensor of the organ;
calculate a first movement evaluation value for at least some of the plurality of images; and
determine a still image from the plurality of images based on the first movement evaluation value and the detection signal of the organ.
2. The endoscope apparatus according to claim 1, wherein the processor is configured to generate
a movement signal based on the detection signal, and the movement evaluation value is evaluated based on the movement signal.
3. The endoscope apparatus according to claim 2, wherein the movement signal has a signal value corresponding to each of the plurality of images.
4. The endoscope apparatus according to claim 2, wherein the processor is configured to calculate the movement evaluation value for each of the plurality of images.
5. The endoscope apparatus according to claim 4,
wherein the processor is configured to
set a first signal value to the movement signal when a movement amount of the organ is smaller than a predetermined amount,
set a second signal value to the movement signal when the movement amount of the organ is larger than the predetermined amount, and
calculate the movement evaluation value by multiplying a weighting coefficient only in a case that the movement signal is the first signal value.
6. The endoscope apparatus according to claim 4,
wherein the processor is configured to
set a first signal value to the movement signal when a movement amount of the organ is smaller than a predetermined amount,
set a second signal value to the movement signal when the movement amount of the organ is larger than the predetermined amount,
calculate the movement evaluation value by
multiplying a first weighting coefficient when a signal value of the movement signal corresponding to the image is the first signal value, and
multiplying a second weighting coefficient larger than the first weighting coefficient when the signal value of the movement signal corresponding to the image is the second signal value.
7. The endoscope apparatus according to claim 4,
wherein the processor is configured to
set a first signal value to the movement signal when a movement amount of the organ is smaller than a first movement amount,
set a second signal value to the movement signal when the movement amount of the organ is larger than the first movement amount and smaller than a second movement amount,
set a third signal value to the movement signal when the movement amount of the organ is larger than a third movement amount, and
calculate the movement evaluation value by
multiplying a first weighting coefficient when a signal value of the movement signal corresponding to the image is the first signal value,
multiplying a second weighting coefficient larger than the first weighting coefficient when the signal value of the movement signal corresponding to the image is the second signal value, and
multiplying a third weighting coefficient larger than the second weighting coefficient when the signal value of the movement signal corresponding to the image is the third signal value.
8. The endoscope apparatus according to claim 4,
wherein the processor is configured to determine
a minimum movement evaluation value from the movement evaluation value in plurality.
9. The endoscope apparatus according to claim 8,
wherein the processor is configured to determine the minimum movement evaluation value excluding the movement evaluation value for which the signal value of the movement signal is a predetermined signal value.

10. The endoscope apparatus according to claim 4,
wherein the plurality of images are captured up in an RGB frame-sequential manner, and
the movement evaluation value of each image is a value calculated based on a color shift amount of RGB.

11. The endoscope apparatus according to claim 4,
wherein the plurality of images are captured by the image sensor for which RGB pixels are arranged on a same plane, and
the movement evaluation value is a value calculated based on a blurring amount.

12. The endoscope apparatus according to claim 4, comprising
a memory,
wherein the memory stores the plurality of images, the movement evaluation value corresponding to each of the plurality of images, and a signal value of the movement signal.

13. The endoscope apparatus according to claim 12,
wherein the processor is configured to
set a first signal value to the movement signal when a movement amount of the organ is smaller than a predetermined amount,
set a second signal value to the movement signal when the movement amount of the organ is larger than the predetermined amount, and
store the image in the memory when the signal value of the movement signal corresponding to the image is the first signal value.

14. The endoscope apparatus according to claim 12,
wherein the processor is configured to
set a first signal value to the movement signal when a movement amount of the organ is smaller than a first movement amount,
set a second signal value to the movement signal when the movement amount of the organ is larger than the first movement amount and smaller than a second movement amount,
set a third signal value to the movement signal when the movement amount of the organ is larger than a third movement amount, and
calculate the movement evaluation value by
multiplying a fourth weighting coefficient when a signal value of the movement signal corresponding to the image is the first signal value, and
multiplying a fifth weighting coefficient larger than the fourth weighting coefficient when the signal value of the movement signal corresponding to the image is the second signal value, and
stores the movement evaluation value in the memory.

15. The endoscope apparatus according to claim 1,
wherein the processor is further configured to calculate a second movement evaluation value, by weighing the first movement evaluation value according to the detection signal of the sensor, and determine a still image from the plurality of images based on the second movement evaluation value.

16. An endoscope apparatus comprising:
a heart rate sensor configured to contact a subject's skin and detect a movement of an organ of the subject and the sensor configured to output a detection signal of the organ;
an endoscope configured for insertion into the subject, the scope comprising an image sensor configured to capture a plurality of images of the organ; and
a processor comprising hardware, the processor operably connected to the heart rate sensor and the image sensor, the processor configured to:
receive a plurality of images, each of the plurality of images captured by the image sensor of the organ;
store a plurality of selected images, the plurality of selected images being selected from the plurality of images according to the detection signal of the detector;
determine a suitable still image from the plurality of selected images based on the detection signal.

* * * * *